(12) United States Patent
Smith et al.

(10) Patent No.: US 10,172,678 B2
(45) Date of Patent: *Jan. 8, 2019

(54) METHOD AND SYSTEM FOR PERFORMING INVASIVE MEDICAL PROCEDURES USING A SURGICAL ROBOT

(71) Applicant: GLOBUS MEDICAL, INC., Audubon, PA (US)

(72) Inventors: David W. Smith, Scottsdale, AZ (US); Regina DeSanctis-Smith, Scottsdale, AZ (US); Alan M. Pitt, Phoenix, AZ (US); Nicholas Theodore, Phoenix, AZ (US); Neil Crawford, Tempe, AZ (US)

(73) Assignee: GLOBUS MEDICAL, INC., Audubon, PA (US)

( * ) Notice: Subject to any disclaimer, the term of this patent is extended or adjusted under 35 U.S.C. 154(b) by 38 days.

This patent is subject to a terminal disclaimer.

(21) Appl. No.: 14/729,096

(22) Filed: Jun. 3, 2015

(65) Prior Publication Data
US 2015/0335386 A1 Nov. 26, 2015

Related U.S. Application Data

(63) Continuation of application No. 13/542,560, filed on Jul. 5, 2012, now Pat. No. 9,078,685, which is a (Continued)

(51) Int. Cl.
| A61B 34/30 | (2016.01) |
| A61B 34/20 | (2016.01) |
| A61B 5/06 | (2006.01) |
| A61B 90/10 | (2016.01) |
| A61B 34/00 | (2016.01) |
| A61B 90/00 | (2016.01) |
| A61B 90/11 | (2016.01) |
| A61B 17/34 | (2006.01) |
| A61B 34/10 | (2016.01) |

(52) U.S. Cl.
CPC ............... *A61B 34/30* (2016.02); *A61B 5/06* (2013.01); *A61B 34/20* (2016.02); *A61B 34/73* (2016.02); *A61B 90/10* (2016.02); *A61B 90/11* (2016.02); *A61B 90/36* (2016.02); *A61B 17/3478* (2013.01); *A61B 34/25* (2016.02); *A61B 2034/107* (2016.02); *A61B 2034/2051* (2016.02); *A61B 2034/301* (2016.02)

(58) Field of Classification Search
None
See application file for complete search history.

(56) References Cited

U.S. PATENT DOCUMENTS 5,354,314 A 10/1994 Hardy et al.
5,397,323 A 3/1995 Taylor et al.
(Continued)

OTHER PUBLICATIONS

US 8,231,638, 07/2012, Swarup et al. (withdrawn)

*Primary Examiner* — Angela M Hoffa

(57) ABSTRACT

A method and system for performing invasive procedures includes a surgical robot which is controlled by a guidance system that uses time of flight calculations from RF transmitters embedded in the robot, surgical instrument, and patient anatomy. Sensors around the room detect RF transmissions emitted by the RF transmitters and drive the robot according to a preprogrammed trajectory entered into the guidance system.

14 Claims, 11 Drawing Sheets

Related U.S. Application Data continuation of application No. 11/845,557, filed on Aug. 27, 2007, now Pat. No. 8,219,178, which is a continuation-in-part of application No. 11/838,027, filed on Aug. 13, 2007, now Pat. No. 8,219,177, which is a continuation-in-part of application No. 11/676,023, filed on Feb. 16, 2007, now Pat. No. 8,010,181.

(56) References Cited

U.S. PATENT DOCUMENTS

| | | | |
|---|---|---|---|
| 5,772,594 | A | 6/1998 | Barrick |
| 5,791,908 | A | 8/1998 | Gillio |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |
| 5,951,475 | A | 9/1999 | Gueziec et al. |
| 6,012,216 | A | 1/2000 | Esteves et al. |
| 6,033,415 | A | 3/2000 | Mittelstadt et al. |
| 6,080,181 | A | 6/2000 | Jensen et al. |
| 6,106,511 | A | 8/2000 | Jensen |
| 6,122,541 | A | 9/2000 | Cosman et al. |
| 6,157,853 | A | 12/2000 | Blume et al. |
| 6,167,145 | A | 12/2000 | Foley et al. |
| 6,167,292 | A | 12/2000 | Badano et al. |
| 6,201,984 | B1 | 3/2001 | Funda et al. |
| 6,205,411 | B1 | 3/2001 | DiGioia, III et al. |
| 6,212,419 | B1 | 4/2001 | Blume et al. |
| 6,231,565 | B1 | 5/2001 | Tovey et al. |
| 6,236,875 | B1 | 5/2001 | Bucholz et al. |
| 6,246,900 | B1 | 6/2001 | Cosman et al. |
| 6,301,495 | B1 | 10/2001 | Gueziec et al. |
| 6,312,435 | B1 | 11/2001 | Wallace et al. |
| 6,314,311 | B1 | 11/2001 | Williams et al. |
| 6,322,567 | B1 | 11/2001 | Mittelstadt et al. |
| 6,325,808 | B1 | 12/2001 | Bernard et al. |
| 6,340,363 | B1 | 1/2002 | Bolger et al. |
| 6,377,011 | B1 | 4/2002 | Ben-Ur |
| 6,379,302 | B1 | 4/2002 | Kessman et al. |
| 6,402,762 | B2 | 6/2002 | Hunter et al. |
| 6,424,885 | B1 | 7/2002 | Niemeyer et al. |
| 6,447,503 | B1 | 9/2002 | Wynne et al. |
| 6,451,027 | B1 | 9/2002 | Cooper et al. |
| 6,477,400 | B1 | 11/2002 | Barrick |
| 6,484,049 | B1 | 11/2002 | Seeley et al. |
| 6,490,467 | B1 | 12/2002 | Bucholz et al. |
| 6,490,475 | B1 | 12/2002 | Seeley et al. |
| 6,499,488 | B1 | 12/2002 | Hunter et al. |
| 6,507,751 | B2 | 1/2003 | Blume et al. |
| 6,535,756 | B1 | 3/2003 | Simon et al. |
| 6,560,354 | B1 | 5/2003 | Maurer, Jr. et al. |
| 6,565,554 | B1 | 5/2003 | Niemeyer |
| 6,587,750 | B2 | 7/2003 | Gerbi et al. |
| 6,614,453 | B1 | 9/2003 | Suri et al. |
| 6,636,757 | B1 | 10/2003 | Jascob et al. |
| 6,645,196 | B1 | 11/2003 | Nixon et al. |
| 6,669,635 | B2 | 12/2003 | Kessman et al. |
| 6,701,173 | B2 | 3/2004 | Nowinski et al. |
| 6,738,656 | B1 * | 5/2004 | Ferre .................. A61B 5/06 600/426 |
| 6,782,287 | B2 | 8/2004 | Grzeszczuk et al. |
| 6,783,524 | B2 | 8/2004 | Anderson et al. |
| 6,786,896 | B1 | 9/2004 | Madhani et al. |
| 6,788,018 | B1 | 9/2004 | Blumenkranz |
| 6,804,581 | B2 | 10/2004 | Wang et al. |
| 6,823,207 | B1 | 11/2004 | Jensen et al. |
| 6,827,351 | B2 | 12/2004 | Graziani et al. |
| 6,837,892 | B2 | 1/2005 | Shoham |
| 6,839,612 | B2 | 1/2005 | Sanchez et al. |
| 6,856,826 | B2 | 2/2005 | Seeley et al. |
| 6,856,827 | B2 | 2/2005 | Seeley et al. |
| 6,879,880 | B2 | 4/2005 | Nowlin et al. |
| 6,892,090 | B2 | 5/2005 | Verard et al. |
| 6,920,347 | B2 | 7/2005 | Simon et al. |
| 6,968,224 | B2 | 11/2005 | Kessman et al. |
| 6,978,166 | B2 | 12/2005 | Foley et al. |
| 6,991,627 | B2 | 1/2006 | Madhani et al. |
| 6,999,852 | B2 | 2/2006 | Green |
| 7,007,699 | B2 | 3/2006 | Martinelli et al. |
| 7,063,705 | B2 | 6/2006 | Young et al. |
| 7,072,707 | B2 | 7/2006 | Galloway, Jr. et al. |
| 7,083,615 | B2 | 8/2006 | Peterson et al. |
| 7,097,640 | B2 | 8/2006 | Wang et al. |
| 7,130,676 | B2 | 10/2006 | Barrick |
| 7,139,418 | B2 | 11/2006 | Abovitz et al. |
| 7,139,601 | B2 | 11/2006 | Bucholz et al. |
| 7,155,316 | B2 | 12/2006 | Sutherland et al. |
| 7,164,968 | B2 | 1/2007 | Treat et al. |
| 7,167,738 | B2 | 1/2007 | Schweikard et al. |
| 7,169,141 | B2 | 1/2007 | Brock et al. |
| 7,172,627 | B2 | 2/2007 | Fiere et al. |
| 7,239,940 | B2 | 7/2007 | Wang et al. |
| 7,248,914 | B2 | 7/2007 | Hastings et al. |
| 7,302,288 | B1 | 11/2007 | Schellenberg |
| 7,313,430 | B2 | 12/2007 | Urquhart et al. |
| 7,318,827 | B2 | 1/2008 | Leitner et al. |
| 7,319,897 | B2 | 1/2008 | Leitner et al. |
| 7,327,865 | B2 | 2/2008 | Fu et al. |
| 7,331,967 | B2 | 2/2008 | Lee et al. |
| 7,333,642 | B2 | 2/2008 | Green |
| 7,339,341 | B2 | 3/2008 | Oleynikov et al. |
| 7,366,562 | B2 | 4/2008 | Dukesherer et al. |
| 7,379,790 | B2 | 5/2008 | Toth et al. |
| 7,386,365 | B2 | 6/2008 | Nixon |
| 7,422,592 | B2 | 9/2008 | Morley et al. |
| 7,435,216 | B2 | 10/2008 | Kwon et al. |
| 7,440,793 | B2 | 10/2008 | Chauhan et al. |
| 7,466,303 | B2 | 12/2008 | Yi et al. |
| 7,493,153 | B2 | 2/2009 | Ahmed et al. |
| 7,505,617 | B2 | 3/2009 | Fu et al. |
| 7,533,892 | B2 | 5/2009 | Schena et al. |
| 7,542,791 | B2 | 6/2009 | Mire et al. |
| 7,555,331 | B2 | 6/2009 | Viswanathan |
| 7,567,834 | B2 | 7/2009 | Clayton et al. |
| 7,594,912 | B2 | 9/2009 | Cooper et al. |
| 7,606,613 | B2 | 10/2009 | Simon et al. |
| 7,607,440 | B2 | 10/2009 | Coste-Maniere et al. |
| 7,630,752 | B2 | 12/2009 | Viswanathan |
| 7,630,753 | B2 | 12/2009 | Simon et al. |
| 7,643,862 | B2 | 1/2010 | Schoenefeld |
| 7,660,623 | B2 | 2/2010 | Hunter et al. |
| 7,689,320 | B2 | 3/2010 | Prisco et al. |
| 7,691,098 | B2 | 4/2010 | Wallace et al. |
| 7,702,379 | B2 | 4/2010 | Avinash et al. |
| 7,711,406 | B2 | 5/2010 | Kuhn et al. |
| 7,720,523 | B2 | 5/2010 | Omernick et al. |
| 7,742,801 | B2 | 6/2010 | Neubauer et al. |
| 7,751,865 | B2 | 7/2010 | Jascob et al. |
| 7,762,825 | B2 | 7/2010 | Burbank et al. |
| 7,763,015 | B2 | 7/2010 | Cooper et al. |
| 7,787,699 | B2 | 8/2010 | Mahesh et al. |
| 7,818,044 | B2 | 10/2010 | Dukesherer et al. |
| 7,819,859 | B2 | 10/2010 | Prisco et al. |
| 7,824,401 | B2 | 11/2010 | Manzo et al. |
| 7,831,294 | B2 | 11/2010 | Viswanathan |
| 7,834,484 | B2 | 11/2010 | Sartor |
| 7,835,557 | B2 | 11/2010 | Kendrick et al. |
| 7,835,778 | B2 | 11/2010 | Foley et al. |
| 7,835,784 | B2 | 11/2010 | Mire et al. |
| 7,840,253 | B2 | 11/2010 | Tremblay et al. |
| 7,840,256 | B2 | 11/2010 | Lakin et al. |
| 7,843,158 | B2 | 11/2010 | Prisco |
| 7,844,320 | B2 | 11/2010 | Shahidi |
| 7,853,305 | B2 | 12/2010 | Simon et al. |
| 7,865,269 | B2 | 1/2011 | Prisco et al. |
| D631,966 | S | 2/2011 | Perloff et al. |
| 7,879,045 | B2 | 2/2011 | Gielen et al. |
| 7,881,767 | B2 | 2/2011 | Strommer et al. |
| 7,881,770 | B2 | 2/2011 | Melkent et al. |
| 7,886,743 | B2 | 2/2011 | Cooper et al. |
| RE42,194 | E | 3/2011 | Foley et al. |
| RE42,226 | E | 3/2011 | Foley et al. |
| 7,907,166 | B2 | 3/2011 | Lamprecht et al. |

(56) References Cited

U.S. PATENT DOCUMENTS

| | | |
|---|---|---|
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,010,181 B2 * | 8/2011 | Smith ............ A61B 5/06 600/411 |
| 8,035,685 B2 | 10/2011 | Jensen |
| 8,046,054 B2 | 10/2011 | Kim et al. |
| 8,046,057 B2 | 10/2011 | Clarke |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,092,370 B2 | 1/2012 | Roberts et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,120,301 B2 | 2/2012 | Goldberg et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,988 B2 | 6/2012 | Jensen |
| 8,219,177 B2 * | 7/2012 | Smith ............ A61B 5/06 600/411 |
| 8,219,178 B2 * | 7/2012 | Smith ............ A61B 5/06 600/411 |
| 8,220,468 B2 | 7/2012 | Cooper et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |

(56) References Cited

U.S. PATENT DOCUMENTS

| | | |
|---|---|---|
| 8,693,730 B2 | 4/2014 | Umasuthan et al. |
| 8,694,075 B2 | 4/2014 | Groszmann et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,734,432 B2 | 5/2014 | Tuma et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,792,704 B2 | 7/2014 | Isaacs |
| 8,800,838 B2 | 8/2014 | Shelton, IV |
| 8,808,164 B2 | 8/2014 | Hoffman et al. |
| 8,812,077 B2 | 8/2014 | Dempsey |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 9,078,685 B2 * | 7/2015 | Smith ................ A61B 5/06 |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0111704 A1 | 5/2006 | Brennerman et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0197896 A1 * | 8/2007 | Moll ................ A61B 1/00039 600/407 |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0046668 A1 | 2/2012 | Gantes |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |

(56) References Cited

U.S. PATENT DOCUMENTS

| | | |
|---|---|---|
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feikas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345718 A1* | 12/2013 | Crawford ............. A61B 17/025 606/130 |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |

\* cited by examiner

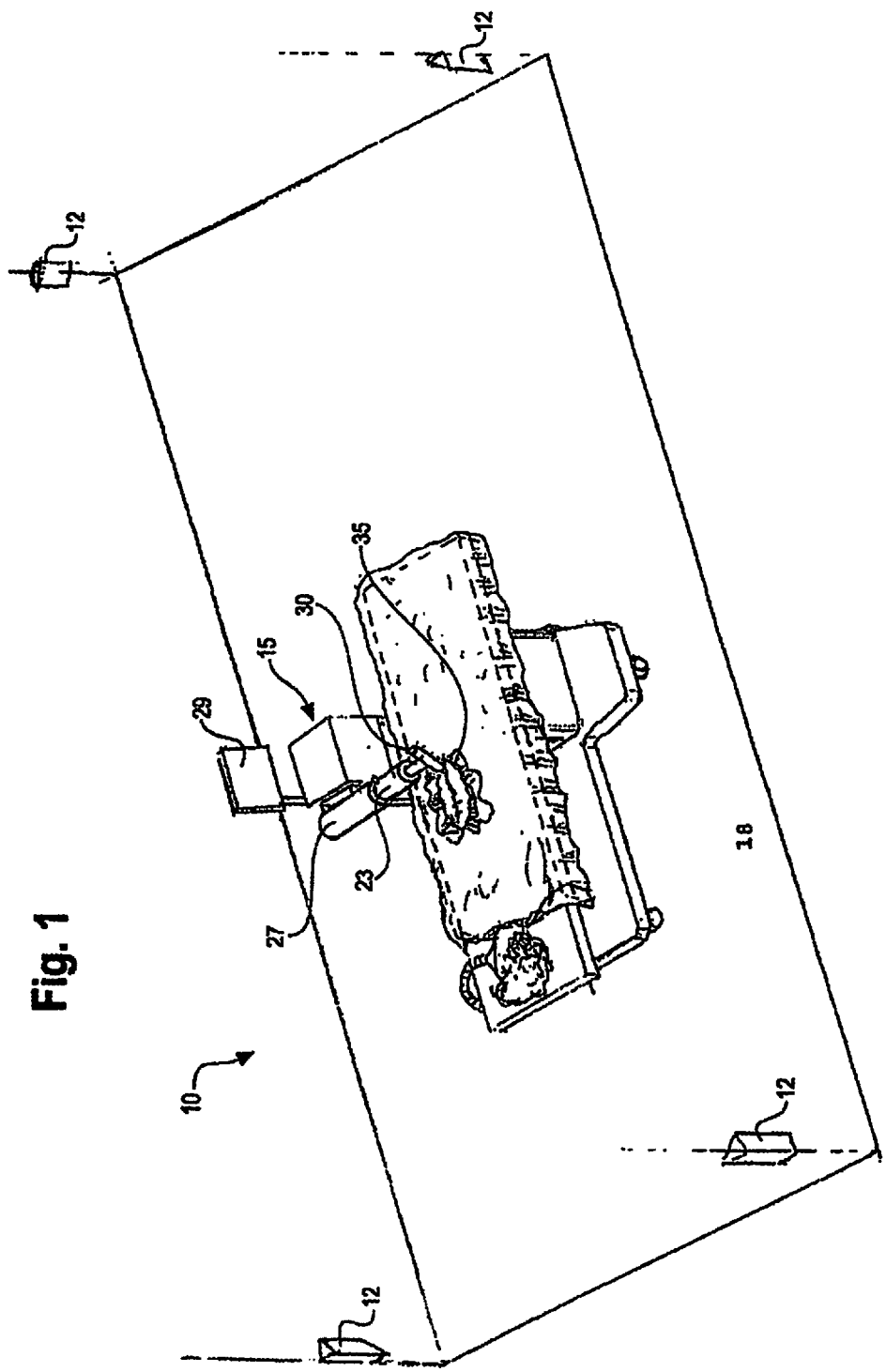

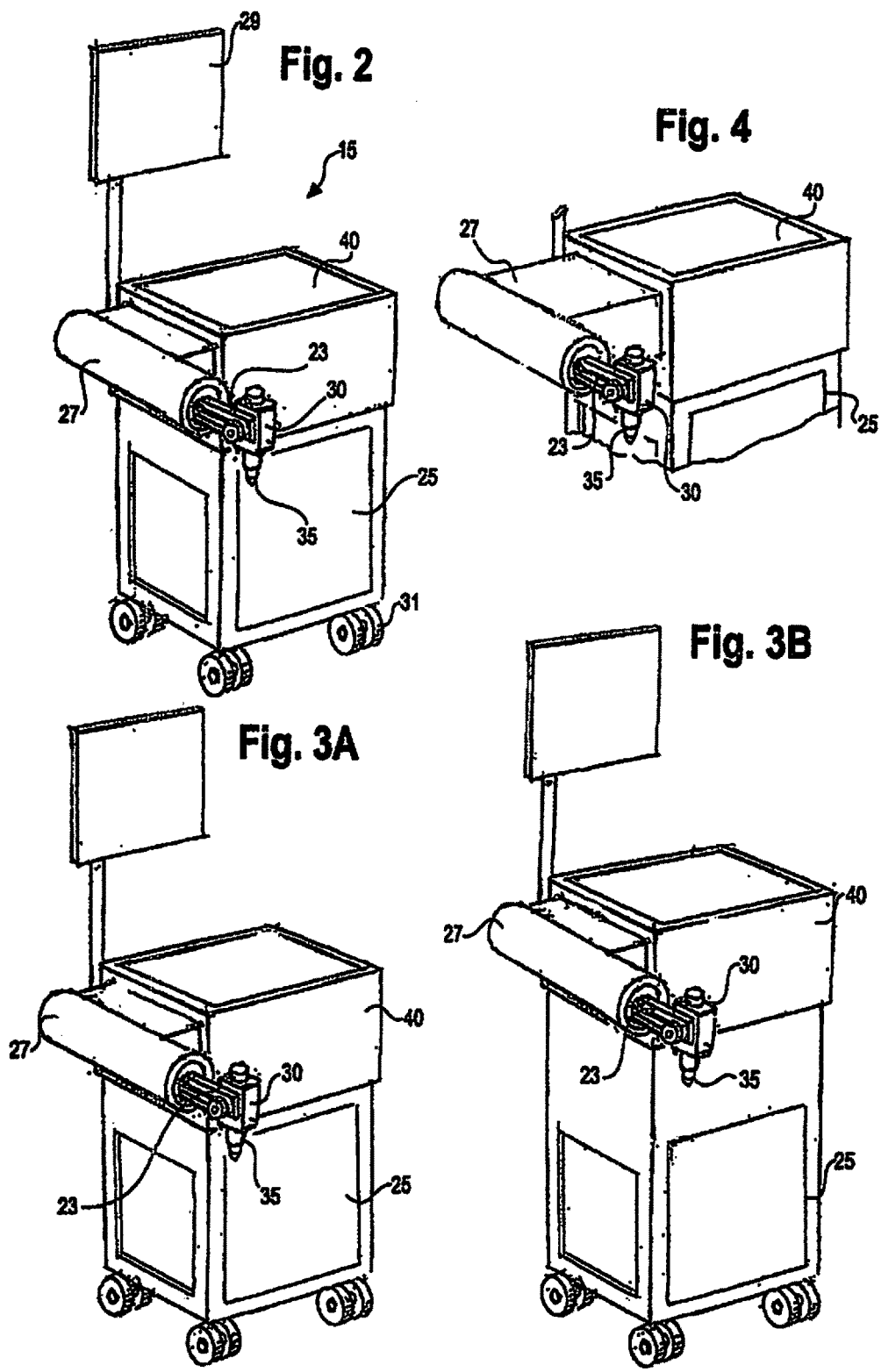

METHOD AND SYSTEM FOR PERFORMING INVASIVE MEDICAL PROCEDURES USING A SURGICAL ROBOT

CROSS-REFERENCE TO RELATED APPLICATIONS

This application is a continuation of U.S. patent application Ser. No. 13/542,560, filed Jul. 5, 2012, which is a continuation of U.S. patent application Ser. No. 11/845,557, filed Aug. 27, 2007, now U.S. Pat. No. 8,219,178, which is a continuation-in-part of U.S. patent application Ser. No. 11/838,027, filed Aug. 13, 2007, now U.S. Pat. No. 8,219,177, which is a continuation-in-part of U.S. application Ser. No. 11/676,023, filed Feb. 16, 2007, now U.S. Pat. No. 8,010,181. This application is related to, but does not claim priority to U.S. Provisional Patent Application Nos. 60/775,816 and 60/774,586, both of which were filed on Feb. 16, 2006. The contents of all applications are hereby incorporated by reference in their entireties for all purposes.

FIELD OF THE INVENTION

This invention generally relates to the use of robots in medical procedures and, more particularly, to a method and system of controlling the movement of an end effectuator disposed on a robot arm by means of, for example, time of flight measurements of radio frequency ("RF") signals that are emitted from inside a patient and that are received by at least three RF receivers positioned near where the procedure is taking place.

BACKGROUND OF THE INVENTION

Various medical procedures require the precise localization of a three dimensional position of a surgical instrument within the body in order to effect optimized treatment. For example, some surgical procedures to fuse vertebrae require that a surgeon drill multiple holes into the bone structure at precise locations. To achieve high levels of mechanical integrity in the fusing system and to balance the forces created in the bone structure it is necessary that the holes are drilled at the correct precise location. Vertebrae, like most bone structures, have complex shapes made up of non-planar curved surfaces making precise and perpendicular drilling difficult. Conventionally, a surgeon manually holds and positions a drill guide tube by using a guidance system to overlay the drill tube's position onto a three dimensional image of the bone structure. This manual process is both tedious and time consuming. The success of the surgery is largely dependent upon the dexterity of the surgeon who performs it.

Limited robotic assistance for surgical procedures is currently available. For example, the da Vinci medical robot system is a robot used in certain surgical applications. In the da Vinci system, the user controls manipulators that control a robotic actuator. The system converts the surgeon's gross movements into micro-movements of the robotic actuator. Although the da Vinci system eliminates hand tremor and provides the user with the ability to work through a small opening, like many of the robots commercially available today, it is expensive, obtrusive, and the setup is cumbersome. Further, for procedures such as thoracolumbar pedicle screw insertion, these conventional methods are known to be error-prone and tedious.

One of the characteristics of the da Vinci system which makes it error prone is that, like many of the current robots used in surgical applications, it uses an articular arm based on a series of rotational joints. The use of an articular system creates difficulties in arriving at a precisely targeted location because the level of any error is increased over each joint in the articular system.

SUMMARY OF INVENTION

In one embodiment, the present invention provides a surgical robot and an imaging system that utilize a Cartesian positioning system as opposed to an articular positioning system. This feature allows, for example, the movement of an effectuator element that forms or is attached to the end of a surgical robot to be individually controlled on the x, y and z axes. This feature also allows the roll, pitch and yaw of the effectuator element to be controlled without creating movement on the x, y or z axes.

The effectuator element can include a leading edge that is either beveled or non-beveled. In an exemplary embodiment, a non-beveled effectuator element is employed that is capable of ablating a pathway through tissue to reach the target position and will not be subjected to the mechanical forces and deflection created by a typical bevel tissue cutting system. In accordance with an exemplary embodiment, a surgical robot includes three linear motors that separately control movement of the effectuator element on the x, y and z axes. These separate motors allow, for example, a degree of precision to be obtained that is not provided by conventional surgical robots. This aspect of the invention gives the surgeon the capability of exactly determining position and strike angles on a three dimensional image.

Another exemplary aspect of the present invention involves the use of at least one RF transmitter that is mounted on an effectuator element of the surgical robot or on a medical instrument that is held by the effectuator element. Three or more RF receivers are mounted in the vicinity of the surgical robot. The precise location of the RF transmitter and, therefore, the surgical instrument formed or held by the end effectuator can be precisely determined by analyzing the RF signals that are emitted from the RF transmitter. By measuring the time of flight of the RF signal from the transmitter to the RF receivers that are positioned at known locations, the position of the end effectuator element with respect to a patient can be determined. A doctor or surgeon can utilize this aspect of the present invention to, for example, perform epidural injections of steroids into a patient to alleviate back pain without the use of x-rays as is currently done with x-ray fluoroscopic techniques.

A still further exemplary aspect of the present invention involves the use of RF feedback to actively control the movement of a surgical robot. To do this control, RF signals are sent by the RF transmitter on an iterative basis and then analyzed in an iterative process to allow, for example, the surgical robot to automatically move the effectuator element to a desired location within a patient's body. The location of the effectuator element and surgical instrument are dynamically updated and can be, for example, displayed to a user in real-time.

The present invention also contemplates a system where RF transmitters are disposed on other elements of the surgical robot, or anywhere within the room where the invasive procedure is taking place, in order to track other devices.

The present invention also contemplates a system where RF transmitters are disposed on the anatomical part of the patient that is the target of the invasive procedure. This system can be used, for example, to correct the movement of the surgical robot in the event the anatomical target moves during the procedure.

In one embodiment, the present invention contemplates a new mechanical system, new component development and improved imaging methods designed with an integrated software architecture that would combine image guidance, medical imaging and a robotic positioning system.

The current invention also contemplates a system that will automatically position and rigidly hold, for example, a guide tube that is precisely aligned with the required trajectory of a pedicle screw during pedicle screw insertion procedures.

BRIEF DESCRIPTION OF THE DRAWINGS

The benefits and advantages of the present invention will become more readily apparent to those of ordinary skill in the relevant art after reviewing the following detailed description and accompanying drawings, wherein:

FIG. 1 is a partial perspective view of a room in which an invasive medical procedure is taking place by means of a surgical robot the movement of which is controlled by analysis of RF signals that are emitted from an inside the patent and received by RF receivers mounted therein;

FIG. 2 is a perspective view of a surgical robot according to an embodiment of the present invention;

FIGS. 3A & 3B are perspective views of the surgical robot illustrated in FIG. 2, which show the movement of the base of the surgical robot in the z-axis direction;

FIG. 4 is a partial perspective view of the surgical robot of FIG. 2 which shows how the robot arm can be moved in the x-axis direction;

DETAILED DESCRIPTION OF THE INVENTION

Figure 5A:
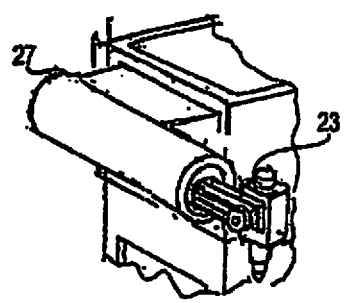
FIGS. 5A & 5B are partial perspective views of the surgical robot of FIG. 2, which show how the robot arm can be moved in the y-axis direction.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated. It should be further understood that the title of this section of this specification, namely, "Detailed Description Of The Invention", relates to a requirement of the United States Patent Office, and does not imply, nor should be inferred to limit the subject matter disclosed herein.

Referring now to FIG. 1, it is seen that in one embodiment of the surgical robot system, a room 10 where an invasive procedure is occurring includes a surgical robot 15, a patient 18 and positioning sensors 12 is provided. Surgical robot 15 includes a display means 29, and a housing 27 which contains a robot arm 23. Robot arm 23 is attached to end effectuator 30. In one embodiment, surgical instrument 35 is removably attached to end effectuator 30. In another embodiment, the end effectuator 30 itself forms an instrument that is used to allow an invasive procedure to take place.

In an embodiment of the invention, prior to an invasive procedure, a 3D image scan is taken of the desired surgical area of patient 18 and sent to a computer (not shown) in communication with surgical robot 15. A physician then programs a desired point of insertion and trajectory for surgical instrument 35 to reach the desired anatomical target in patient 18. This desired point of insertion and trajectory is planned on the 3D image scan which is displayed on display means 29. For example, a physician can plan the desired insertion point and trajectory on a computed tomography (CT) scan of patient 18.

One aspect of the present invention involves the use of a local positioning system (LPS) to track the position of surgical instrument 35. A general description of the LPS system follows. An RF transmitter is affixed at a known location on either the end effectuator 30 or the medical instrument 35. Three transmitters may be evenly radially distributed around the effectuator 30. Three or more RF receivers are positioned at known locations within, for example, the room where the invasive procedure is to take place. Preferably, the RF receivers are not located in the same plane that is parallel to the floor of the room where the procedure is performed.

To calculate the position of the RF transmitter, the time of flight of the RF signal from the RF transmitter to each one of the RF receivers is measured. Because the velocity of the RF signal is known, the time of flight measurements result in at least three distance measurements, one from each RF receiver.

The memory of a control device that performs the time of flight calculations can include, for example, a geometrical description of the location of the RF transmitter with respect to the operative end of the medical instrument 35 or end effectuator 30 that is utilized to perform or assist in performing an invasive procedure. By doing so, the position of the RF transmitter as well as the dimensional profile of the medical instrument or the effectuator element itself can be displayed on a monitor that is viewed by the person performing the invasive procedure. As one example, the end effectuator element 30 can be a tubular element that is positioned at a desired location with respect to, for example, a patient's spine in connection with the performance of a spinal surgery. The tubular element can be aligned with the z axis defined by corresponding robot motor or, for example, can be disposed at an angle relative thereto. In either case, the control device takes the orientation of the tubular element and the position of the RF transmitter into account. The transmitter is affixed at a desired location of the instrument and the control device may be configured to selectively energize the transmitter to cause at least a portion of the instrument to move in a desired direction.

Another aspect of the present invention involves the utilization of a robot that is capable of moving the end effectuator 30 in x, y and z directions that are orthogonal to each other independently of each other or in any combination. For example, the end effectuator 30 can be moved a given distance along the x axis without causing any movement along the y or z axes. The roll, pitch and yaw and the end effectuator 30 also can be selectively controlled. This aspect of the present invention is advantageous because, for example, its use allows invasive medical procedures to take place with a significantly improved accuracy compared to conventional robots that utilize, for example, a six degree of freedom robot arm. A more complete description of these and other aspects of the invention follows.

Referring to FIG. 1, positioning sensors 12 receive RF signals from RF transmitters (not pictured) located within room 10. These RF transmitters are disposed on various points on surgical robot 10 and/or on patient 18. For example, RF transmitters are attached to housing 27, robot arm 23, end effectuator 30 and surgical instrument 35. Positioning sensors 12, which in an exemplary embodiment comprise RF receivers that are in communication with a computer (not pictured), receive the signal from the RF transmitters. Each transmitter transmits on a different frequency so the identity of each transmitter in the room is determinable. The location of the RF transmitters, and consequently the objects to which the transmitters are attached, are calculated by the computer using time of flight algorithms.

The computer (not pictured) is also in communication with surgical robot 15, and moves surgical robot 15 according to the preplanned trajectory entered prior to the procedure. The position of surgical instrument 35 is dynamically updated so that surgical robot 15 is aware of the location of surgical instrument 35 location at all times during the procedure. Consequently, surgical robot 15 can move surgical instrument 35 to the desired position quickly with minimal damage to patient 18 and without any further assistance from a physician unless the physician so desires. Surgical robot 15 can also correct the path if surgical instrument 35 strays from the desired trajectory.

The physician or other user of the system has the option to stop, modify, or manually control the autonomous movement of surgical robot 15. Further, tolerance controls are preprogrammed into surgical robot 15, which adjust the movement of the surgical robot 15 if certain conditions are met. For example, if the surgical robot 15 cannot detect the positions of surgical instrument 35 because of a malfunction in the RF transmitter attached thereto, it will stop movement. Another example is if surgical robot 15 detects a resistance above a tolerance level, then it will stop movement.

In a preferred embodiment of the invention, display means 29 is a monitor attached to surgical robot 15. Alternatively, display means 29 is not attached to surgical robot 15, but is located either within surgical room 10 or in a remote location.

The computer for use in the system (not pictured), can be located within surgical robot 15, or, alternatively, in another location within surgical room 10 or in a remote location. The computer is in conununication with positioning sensors 12 and surgical robot 15.

The surgical robot can also be used with existing guidance systems. Alternative guidance systems are within the scope and spirit of the invention. For instance, an optical tracking system for tracking the location of the surgical device. A commercially available infrared optical tracking system, such as Optotrak (Northern Digital, Waterloo, Ontario, Canada), can be used to track the patient movement and the robot's base location and used with the guidance system. Optical systems require the use of optical markers, which are markers which emit or reflect light, attached to the surgical device. Light emitted from the markers is read by cameras or optical sensors. The location of the object is calculated through triangulation.

Referring now to FIG. 2, it is seen that one embodiment of the surgical robot is shown. The surgical robot includes a base 25 connected to wheels 31. Case 40 is slidably attached to base 25 so that case 40 can slide up and down on a z-axis line perpendicular to the surface on which base 25 sits. Surgical robot also includes a display means 29, and a housing 27 which contains arm 23. Arm 23 is connected to an end effectuator 30. Surgical instrument 35 is removably attached to end effectuator 30.

Surgical instrument 35 can be any instrument used in a medical procedure, both invasive or non-invasive. Surgical instrument 35 may be, for example, a catheter, a probe, a sensor, needle, scalpel forceps, or any other instrument used in a surgical, non-invasive, or diagnostic procedure. Surgical instrument 35 can also be a biological delivery device apparatus, such as a syringe, which can distribute biologically acting compounds throughout the body. The plunger of the syringe may be manually pressed by a user or automatically compressed by the system once the desired target is reached.

The surgical robot is moveable in a plurality of axes in order to improve the ability to precisely reach a target location. The robot moves on a Cartesian positioning system, that is, movements in different axes can occur relatively independently instead of at the end of a series of joints.

Referring now to FIGS. 3A and 3B, the movement of case 40 relative to base 25 is shown. Case 40 can raise and lower relative to the base 25 in the z-axis direction.

In a preferred embodiment of the invention, housing 27 is attached to case 40 and moves in the z-direction with case 40 when case 40 is raised and lowered. Consequently, arm 23, end effectuator 30 and surgical instrument 35 move with case 40 as case 40 is raised and lowered relative to base 25.

Referring now to FIG. 4, housing 27 is slidably attached to case 40 so that it can extend and retract in a x-axis direction relative to case 40 and perpendicular to the direction case 40 moves relative to base 25. Consequently, arm 23, end effectuator 30 and surgical instrument 35 move with housing 27 as housing 27 is extended and retracted relative to case 40.

Figure 5B:
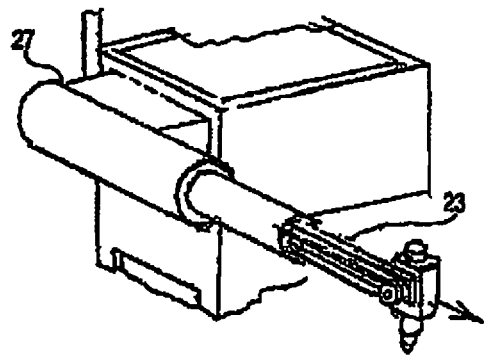

Referring now to FIGS. 5A and 5B, the extension of arm 23 along the y-axis is shown. Arm 23 is extendable on the y-axis relative to case 40, base 25, and housing 27. Consequently, end effectuator 30 and surgical instrument 35 move with arm 23 as arm 23 is extended and retracted relative to housing 27. In an embodiment of the invention, arm 23 is attached to a low profile rail system (not shown) which is encased by housing 27.

Figure 6:
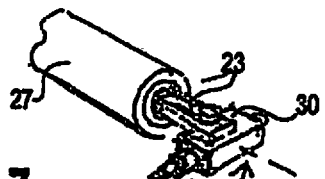
FIG. 6 is a perspective view of a portion of the robot arm of FIG. 2 showing how an effectuator element can be twisted about a y-axis.
Figure 7:
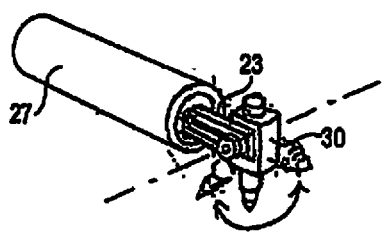
FIG. 7 is a perspective view of a portion of a robot arm of FIG. 2 showing how an effectuator element can be pivoted about a pivot axis that is perpendicular to the y-axis.
Figure 8A:
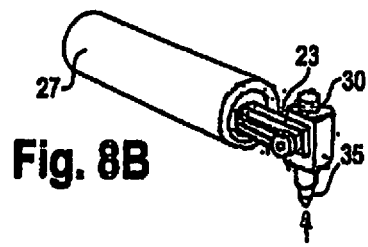
FIGS. 8A & 8B are partial perspective views of the surgical robot of FIG. 2, which show the movement of a surgical instrument along the z-axis from an effectuator element.
Figure 8B:
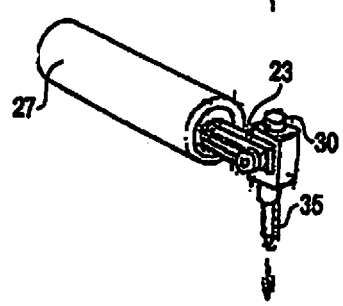

Referring now to FIGS. 6, 7 and 8, the movement of the end effectuator 30 is shown. FIG. 6 shows end effectuator 30 is capable of rotating along the x axis. FIG. 7 shows end effectuator 30 is capable of rotating along the y-axis. FIG. 8 shows end effectuator 30 is capable of raising and lowering surgical instrument 35 on the z axis.

Figure 9:
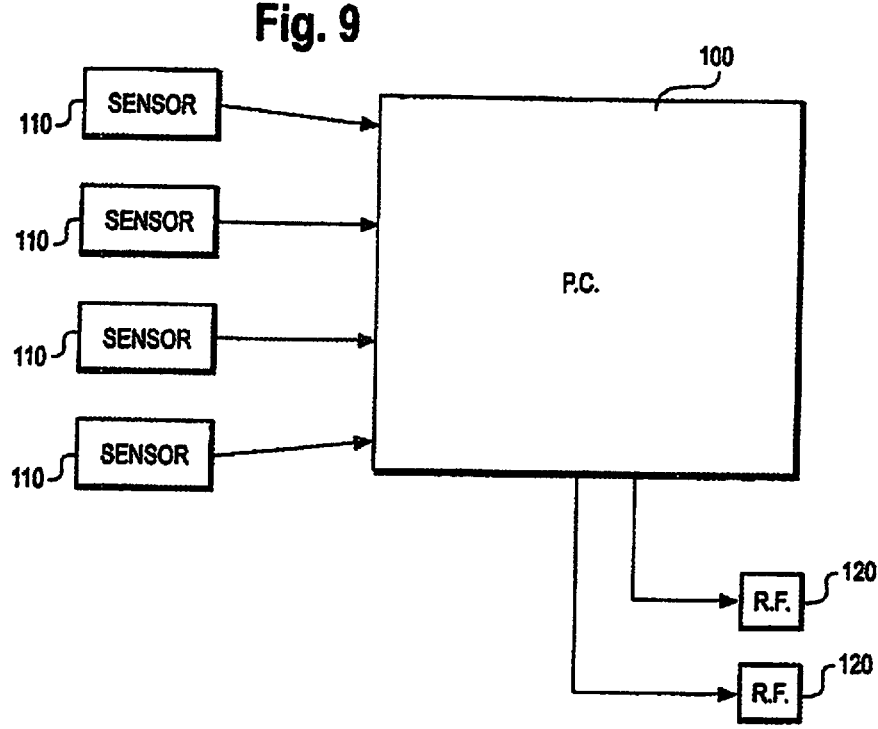
FIG. 9 is a system diagram of which shows the local positioning sensors, controlling PC, and Radiofrequency (RF) transmitter.

Referring now to FIG. 9, a system diagram of the positioning sensors 110, computer 100, and RF transmitters 120 is provided. Computer 100 is in communication with positioning sensors 110. In operation, RF transmitters 120 are attached to various points on the surgical robot. RF transmitters 120 may also be attached to various points on or around the anatomical target. Computer 100 sends a signal through a wired connection to RF transmitters 120, prompting RF transmitters 120 to transmit RF signals. The RF signals are read by positioning sensors 110. Positioning sensors 110 are in communication with computer 100, which calculates the location of the positions of all the RF sensors based on time-of-flight information received from the positioning sensors 110. Computer 100 dynamically updates the calculated location of the surgical device being used in the procedure, which is displayed to the user.

Alternatively, computer 100 can be wirelessly connected to RF transmitters 120.

Figure 10:
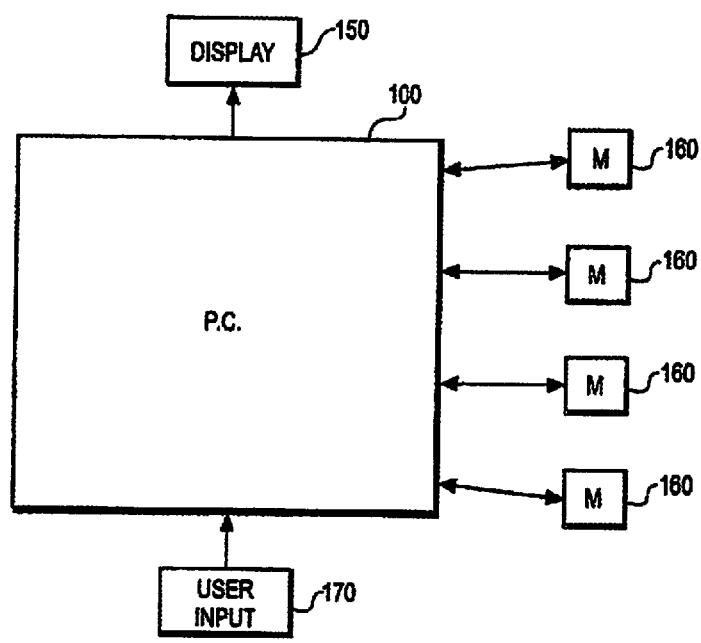
FIG. 10 is a system diagram of the controlling PC, user input, and motors for controlling the robot.

Referring now to FIG. 10, a system diagram of computer 100, display 150, user input 170, and motors 160 is provided. Motors 160 are installed in the surgical robot and control the movement of the surgical robot as described above. Computer 100, which dynamically updates the location of the surgical device being used in the procedure, sends the appropriate signals to the motors 160 so that surgical robot reacts accordingly in response to information received by computer 100. For example, computer 100 prompts motors 160 to move the surgical device along a preplanned trajectory.

The user uses input 170 to plan the trajectory of the desired navigation prior to the invasive procedure. If the user wants to make changes in the invasive procedure after it has commenced, he can use user input 170 to make the desired changes. Computer 100 will then send the appropriate signals to motors 160 in response to the user input.

In a preferred embodiment of the invention, motors 160 are pulse motors providing direct drive, or driving a belt drive and pulley combination attached to the surgical instrument used in the procedure. Alternatively, motors 160 are pulse motors and are attached to a belt drive rack-and-pinion system, or similar power transmission components.

Figure 11:
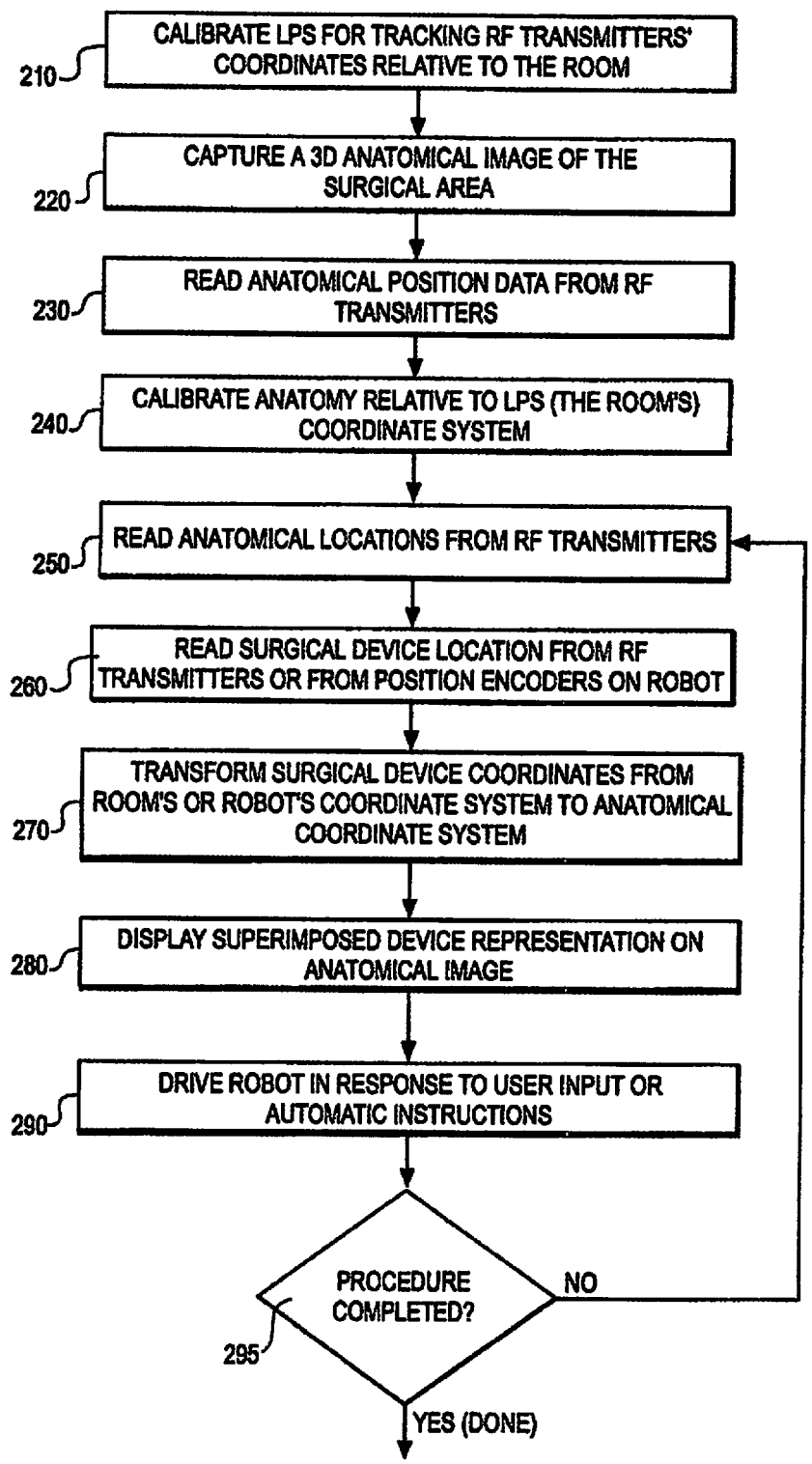
FIG. 11 is a flow chart diagram for general operation of the surgical robot according to an embodiment of the present invention.

Referring now to FIG. 11, a flow chart diagram for general operation of the robot according to an embodiment of the invention is shown.

At step 210, the local positioning system (LPS) establishes a spatial coordinate measuring system for the room where the invasive procedure is to occur; in other words, the LPS is calibrated. In order to calibrate the LPS, a mechanical fixture that includes a plurality of calibrating transmitters attached thereto is placed within the room where positioning sensors are located. At least three calibrating transmitters are required, but any number of calibrating transmitters above three is within the scope of the invention. Also, at least three positioning sensors are required, but any number of positioning sensors above three is also within the scope of the invention, and the accuracy of the system is increased with the addition of more positioning sensors.

The distance between each of the calibrating transmitters relative to each other is measured prior to calibration step 210. Each calibrating transmitter transmits RF signals on a different frequency so the positioning sensors can determine which transmitter emitted a particular RF signal. The signal of each of these transmitters is received by positioning sensors. Since the distance between each of the calibrating transmitters is known, and the sensors can identify the signals from each of the calibrating transmitters based on the known frequency, the positioning sensors are able to calculate, using time of flight calculation, the spatial distance of each of the positioning sensors relative to each other. The system is now calibrated. As a result, the positioning sensors can now determine the spatial position of any new RF transmitter introduced into the room relative to the positioning sensors.

At step 220, a 3D anatomical image scan, such as a CT scan, is taken of the anatomical target. Any 3D anatomical image scan may be used with the surgical robot and is within the scope of the present invention.

At step 230, the positions of the RF transmitters tracking the anatomical target are read by positioning sensors. These transmitters identify the initial position of the anatomical target and any changes in position during the procedure.

If any RF transmitters must transmit through a medium that changes the RF signal characteristics, then the system will compensate for these changes when determining the transmitter's position.

At step 240, the positions of the transmitters on the anatomy are calibrated relative to the LPS coordinate system. In other words, the LPS provides a reference system, and the location of the anatomical target is calculated relative to the LPS coordinates. To calibrate the anatomy relative to the LPS, the positions of transmitters affixed to the anatomical target are recorded at the same time as positions of temporary transmitters on precisely known landmarks on the anatomy that can also be identified on the anatomical image. This calculation is performed by a computer.

At step 250, the positions of the RF transmitters that track the anatomical target are read. Since the locations of the transmitters on the anatomical target have already been calibrated, the system can easily determine if there has been any change in position of the anatomical target.

At step 260, the positions of the transmitters on the surgical instrument are read. The transmitters may be located on the surgical instrument itself, and/or there may be transmitters attached to various points of the surgical robot.

In an embodiment of the invention, the surgical robot also includes a plurality of position encoders attached thereto that help determine the position of the surgical instrument. Position encoders are devices used to generate an electronic signal that indicates a position or movement relative to a reference position. There are many ways to generate a position signal, including for example, magnetic sensors, capacitive sensors, and optical sensors.

Position data read from the position encoders may be used to determine the position of the surgical instrument used in the procedure, and may be redundant of position data calculated from RF transmitters located on the surgical instrument. Therefore, position data from the position encoders may be used to double-check the position being read from the LPS.

At step 270, the coordinates of the positions of the transmitters on the surgical instrument, and/or the positions read from the position encoders, is calibrated relative to the anatomical coordinate system. In other words, the position data of the surgical instrument is synchronized into the same coordinate system as the anatomy. This calculation is performed automatically by the computer since the positions of the transmitters on the anatomical target and the positions of the transmitters on the surgical instrument are in the same coordinate system and the positions of the transmitters on the anatomical target are already calibrated relative to the anatomy.

At step 280, the computer superimposes a representation of the location calculated in step 270 of the surgical device on the 3D anatomical image of the patient taken in step 220. The superimposed image is displayed to the user.

At step 290, the computer sends the appropriate signals to the motors to drive the surgical robot. If the user preprogrammed a trajectory, then the robot is driven so that the surgical instrument follows the preprogrammed trajectory if there is no further input from the user. If there is user input, then the computer drives the robot in response to the user input.

At step 295, the computer determines whether the procedure has been completed. If the procedure has not been completed, then the process beginning at step 250 is repeated.

At any time during the procedure, certain fault conditions may cause the computer to interrupt the program and respond accordingly. For instance, if the signal from the RF transmitters cannot be read, then the computer may be programmed to stop the movement of the robot or remove the surgical instrument from the patient. Another example of a fault condition is if the robot encounters a resistance above a preprogrammed tolerance level. Another example of a fault condition is if the RF transmitters on the anatomical target indicate that the location of the anatomical target has shifted relative to the RF transmitters—this spatial relationship should be fixed. In this case, one indicator that the anatomical target location has shifted relative to the transmitters is if the computer calculates that the surgical instrument appears to be inside bone when no drilling or penetration is actually occurring.

The proper response to each condition may be programmed into the, or a specific response may be user-initiated as well. For example, the computer may determine that in response to an anatomy shift, the anatomy would have to be recalibrated, and the process beginning at step 230 should be repeated. Alternatively, a fault condition may require the flowchart to repeat from step 210. Another alternative is the user may decide that recalibration from step 230 is desired, and initiate that step himself.

Figure 12:
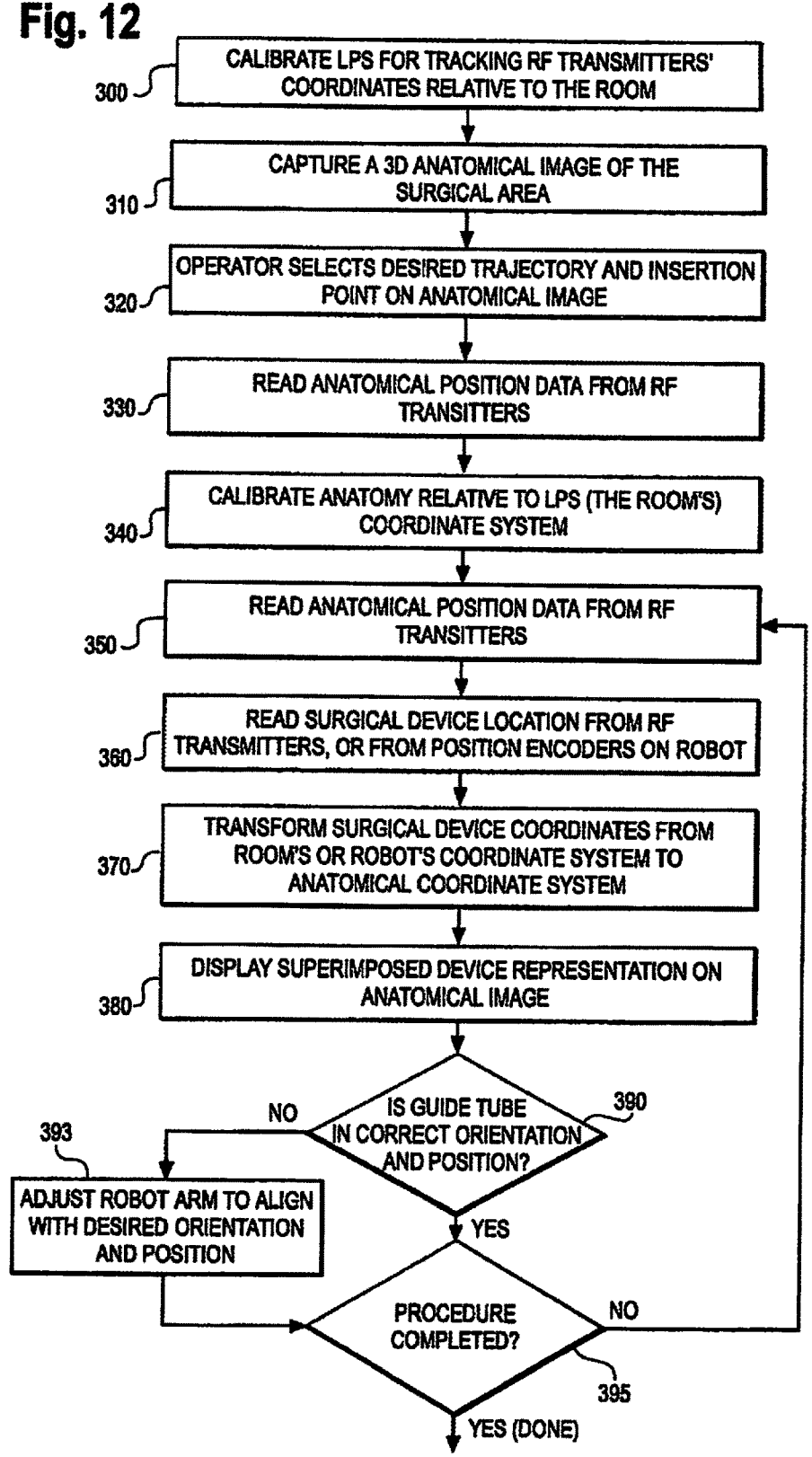
FIG. 12 is a flow chart diagram for a closed screw/needle insertion according to an embodiment of the present invention.

Referring now to FIG. 12, a flow chart diagram for a closed screw/needle insertion procedure according to an embodiment of the invention is shown. In a closed pedicle screw insertion procedure, the robot holds a guide tube adjacent to the patient in the correct angular orientation and at the point where a pedicle screw is to be inserted through the tissue and into the bone of the patient.

The distance between each of the calibrating transmitters relative to each other is measured prior to calibration step 300. Each calibrating transmitter transmits RF signals on a different frequency so the positioning sensors can determine which transmitter emitted a particular RF signal. The signal of each of these transmitters is received by positioning sensors. Since the distance between each of the calibrating transmitters is known, and the sensors can identify the signals from each of the calibrating transmitters based on the known frequency, the positioning sensors are able to calculate, using time of flight calculation, the spatial distance of each of the positioning sensors relative to each other. The system is now calibrated. As a result, the positioning sensors can now determine the spatial position of any new RF transmitter introduced into the room relative to the positioning sensors.

At step 310, a 3D anatomical image scan, such as a CT scan, is taken of the anatomical target. Any 3D anatomical image scan may be used with the surgical robot and is within the scope of the present invention.

At step 320, the operator selects a desired trajectory and insertion point of the surgical instrument on the anatomical image captured at step 310. This desired trajectory and insertion point is programmed into the computer so that the robot can drive a guide tube automatically to follow the trajectory.

At step 330, the positions of the RF transmitters tracking the anatomical target are read by positioning sensors. These transmitters identify the initial position of the anatomical target and any changes in position during the procedure.

If any RF transmitters must transmit through a medium that changes the RF signal characteristics, then the system will compensate for these changes when determining the transmitter's position.

At step 340, the positions of the transmitters on the anatomy are calibrated relative to the LPS coordinate system. In other words, the LPS provides a reference system, and the location of the anatomical target is calculated relative to the LPS coordinates. To calibrate the anatomy relative to the LPS, the positions of transmitters affixed to the anatomical target are recorded at the same time as positions of temporary transmitters on precisely known landmarks on the anatomy that can also be identified on the anatomical image. This calculation is performed by a computer.

At step 350, the positions of the RF transmitters that track the anatomical target are read. Since the locations of the transmitters on the anatomical target have already been calibrated, the system can easily determine if there has been any change in position of the anatomical target.

At step 360, the positions of the transmitters on the surgical instrument are read. The transmitters may be located on the surgical instrument itself, and/or there may be transmitters attached to various points of the surgical robot.

In an embodiment of the invention, the surgical robot also includes a plurality of position encoders attached thereto that help determine the position of the surgical instrument. Position encoders are devices used to generate an electronic signal that indicates a position or movement relative to a reference position. There are many ways to generate a position signal, including for example, magnetic sensors, capacitive sensors, and optical sensors.

Position data read from the position encoders may be used to determine the position of the surgical instrument used in the procedure, and may be redundant of position data calculated from RF transmitters located on the surgical instrument. Therefore, position data from the position encoders may be used to double-check the position being read from the LPS.

At step 370, the coordinates of the positions of the transmitters on the surgical instrument, and/or the positions read from the position encoders, is calibrated relative to the anatomical coordinate system. In other words, the position data of the surgical instrument is synchronized into the same coordinate system as the anatomy. This calculation is performed automatically by the computer since the positions of the transmitters on the anatomical target and the positions of the transmitters on the surgical instrument are in the same coordinate system and the positions of the transmitters on the anatomical target are already calibrated relative to the anatomy.

At step 380, the computer superimposes a representation of the location calculated in step 370 of the surgical device on the 3D anatomical image of the patient taken in step 310. The superimposed image is displayed to the user.

At step 390, the computer determines whether the guide tube is in the correct orientation and position to follow the trajectory planned at step 320. If it is not, then step 393 is reached. If it is in the correct orientation and position to follow the trajectory, then step 395 is reached.

At step 393, the computer determines what adjustments it needs to make in order to make the guide tube follow the preplanned trajectory. The computer sends the appropriate signals to drive the motors in order to correct the movement of the guide tube.

At step 395, the computer determines whether the procedure has been completed. If the procedure has not been completed, then the process beginning at step 350 is repeated.

At any time during the procedure, certain fault conditions may cause the computer to interrupt the program and respond accordingly. For instance, if the signal from the RF transmitters cannot be read, then the computer may be programmed to stop the movement of the robot or lift the guide tube away from the patient. Another example of a fault condition is if the robot encounters a resistance above a preprogrammed tolerance level. Another example of a fault condition is if the RF transmitters on the anatomical target indicate that the location of the anatomical target has shifted relative to the RF transmitters—this spatial relationship should be fixed. In this case, one indicator that the anatomical target location has shifted relative to the transmitters is if the computer calculates that the surgical instrument appears to be inside bone when no drilling or penetration is actually occurring.

The proper response to each condition may be programmed into the, or a specific response may be user-initiated as well. For example, the computer may determine that in response to an anatomy shift, the anatomy would have to be recalibrated, and the process beginning at step 330 should be repeated. Alternatively, a fault condition may require the flowchart to repeat from step 300. Another alternative is the user may decide that recalibration from step 330 is desired, and initiate that step himself.

Figure 13:
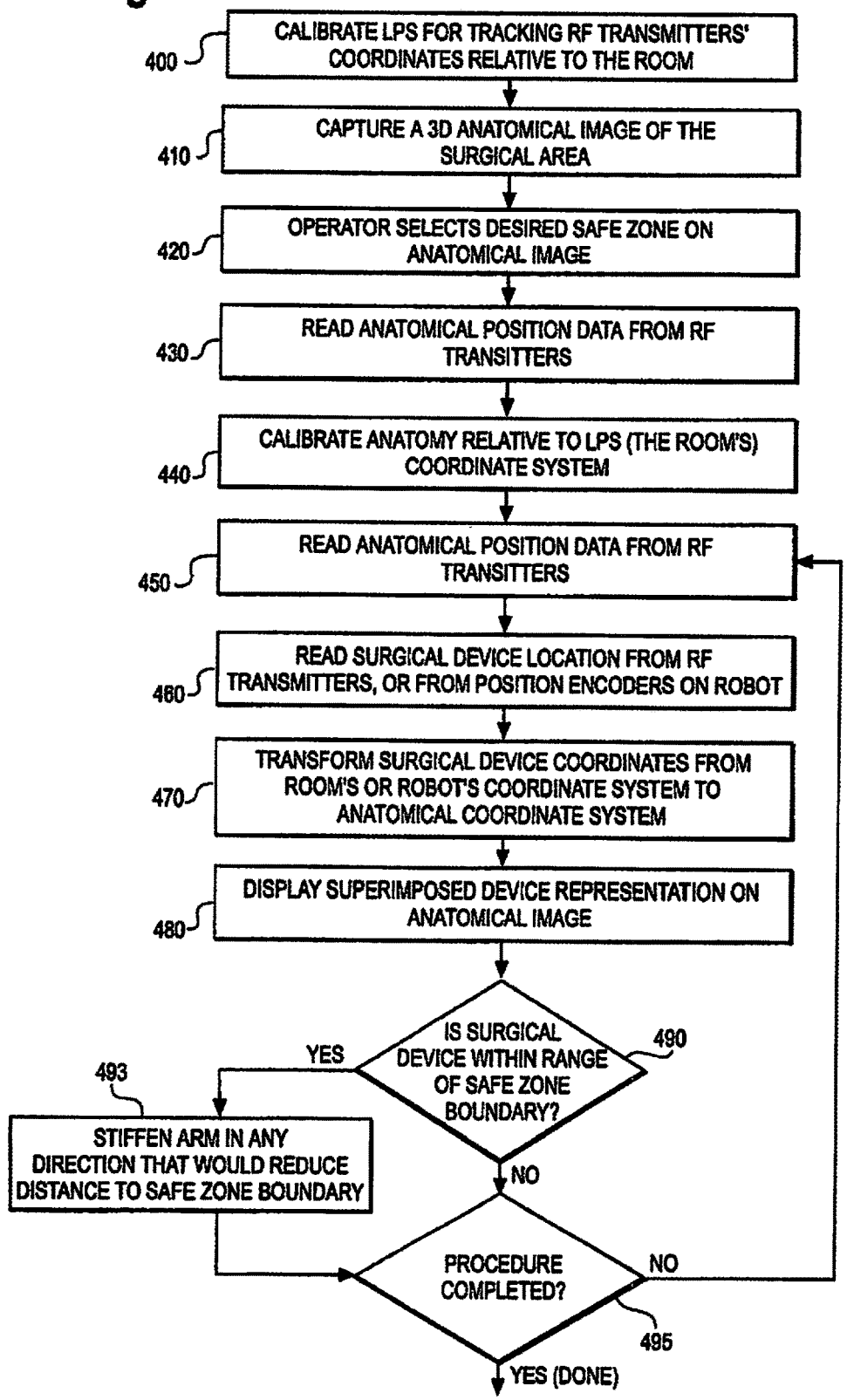
FIG. 13 is a flow chart diagram of a safe zone surgery according to an embodiment of the present invention.

Referring now to FIG. 13, a flow chart diagram for a safe zone surgical procedure according to an embodiment of the invention is shown. In a safe zone surgical procedure, there is a defined "safe zone" around the surgical area within which the surgical device must stay. The physician manually controls the surgical device that is attached to the end effectuator of the surgical robot. If the physician moves the surgical device outside of the safe zone, then the surgical robot stiffens the arm so that the physician cannot move the instrument in any direction that The distance between each of the calibrating transmitters relative to each other is would move the surgical device outside the safe zone.

The distance between each of the calibrating transmitters relative to each other is measured prior to calibration step 400. Each calibrating transmitter transmits RF signals on a different frequency so the positioning sensors can determine which transmitter emitted a particular RF signal. The signal of each of these transmitters is received by positioning sensors. Since the distance between each of the calibrating transmitters is known, and the sensors can identify the signals from each of the calibrating transmitters based on the known frequency, the positioning sensors are able to calculate, using time of flight calculation, the spatial distance of each of the positioning sensors relative to each other. The system is now calibrated. As a result, the positioning sensors can now determine the spatial position of any new RF transmitter introduced into the room relative to the positioning sensors.

At step 410, a 3D anatomical image scan, such as a CT scan, is taken of the anatomical target. Any 3D anatomical image scan may be used with the surgical robot and is within the scope of the present invention.

At step 420, the operator inputs a desired safe zone on the anatomical image taken in step 410. In an embodiment of the invention, the operator uses an input to the computer to draw a safe zone on a CT scan taken of the patient in step 410.

At step 430, the positions of the RF transmitters tracking the anatomical target are read by positioning sensors. These transmitters identify the initial position of the anatomical target and any changes in position during the procedure.

If any RF transmitters must transmit through a medium that changes the RF signal characteristics, then the system will compensate for these changes when determining the transmitter's position.

At step 440, the positions of the transmitters on the anatomy are calibrated relative to the LPS coordinate system. In other words, the LPS provides a reference system, and the location of the anatomical target is calculated relative to the LPS coordinates. To calibrate the anatomy relative to the LPS, the positions of transmitters affixed to the anatomical target are recorded at the same time as positions of temporary transmitters on precisely known landmarks on the anatomy that can also be identified on the anatomical image. This calculation is performed by a computer.

At step 450, the positions of the RF transmitters that track the anatomical target are read. Since the locations of the transmitters on the anatomical target have already been calibrated, the system can easily determine if there has been any change in position of the anatomical target.

At step 460, the positions of the transmitters on the surgical instrument are read. The transmitters may be located on the surgical instrument itself; and/or there may be transmitters attached to various points of the surgical robot. In an embodiment of the invention, the surgical robot also includes a plurality of position encoders attached thereto that help determine the position of the surgical instrument. Position encoders are devices used to generate an electronic signal that indicates a position or movement relative to a reference position. There are many ways to generate a position signal, including for example, magnetic sensors, capacitive sensors, and optical sensors.

Position data read from the position encoders may be used to determine the position of the surgical instrument used in the procedure, and may be redundant of position data calculated from RF transmitters located on the surgical instrument. Therefore, position data from the position encoders may be used to double-check the position being read from the LPS.

At step 470, the coordinates of the positions of the transmitters on the surgical instrument, and/or the positions read from the position encoders, is calibrated relative to the anatomical coordinate system. In other words, the position data of the surgical instrument is synchronized into the same coordinate system as the anatomy. This calculation is performed automatically by the computer since the positions of the transmitters on the anatomical target and the positions of the transmitters on the surgical instrument are in the same coordinate system and the positions of the transmitters on the anatomical target are already calibrated relative to the anatomy.

At step 480, the computer superimposes a representation of the location calculated in step 470 of the surgical device on the 3D anatomical image of the patient taken in step 410. The superimposed image is displayed to the user.

At step 490, the computer determines whether the surgical device attached to the end effectuator of the surgical robot is within a specified range of the safe zone boundary, for example, within 1 millimeter of reaching the safe zone boundary. If the end effectuator is almost to the boundary, then step 493 is reached. If it is well within the safe zone boundary, then step 495 is reached.

At step 493, the computer stiffens the arm of the surgical robot in any direction that would allow the user to move the surgical device closer to the safe zone boundary.

At step 495, the computer determines whether the procedure has been completed. If the procedure has not been completed, then the process beginning at step 450 is repeated.

At any time during the procedure, certain fault conditions may cause the computer to interrupt the program and respond accordingly. For instance, if the signal from the RF transmitters cannot be read, then the computer may be programmed to stop the movement of the robot or remove the surgical instrument from the patient. Another example of a fault condition is if the robot encounters a resistance above a preprogrammed tolerance level. Another example of a fault condition is if the RF transmitters on the anatomical target indicate that the location of the anatomical target has shifted relative to the RF transmitters—this spatial relationship should be fixed. In this case, one indicator that the anatomical target location has shifted relative to the transmitters is if the computer calculates that the surgical instrument appears to be inside bone when no drilling or penetration is actually occurring.

The proper response to each condition may be programmed into the, or a specific response may be user-initiated as well. For example, the computer may determine that in response to an anatomy shift, the anatomy would have to be recalibrated, and the process beginning at step 430 should be repeated. Alternatively, a fault condition may require the flowchart to repeat from step 400. Another alternative is the user may decide that recalibration from step 430 is desired, and initiate that step himself.

Figure 14:
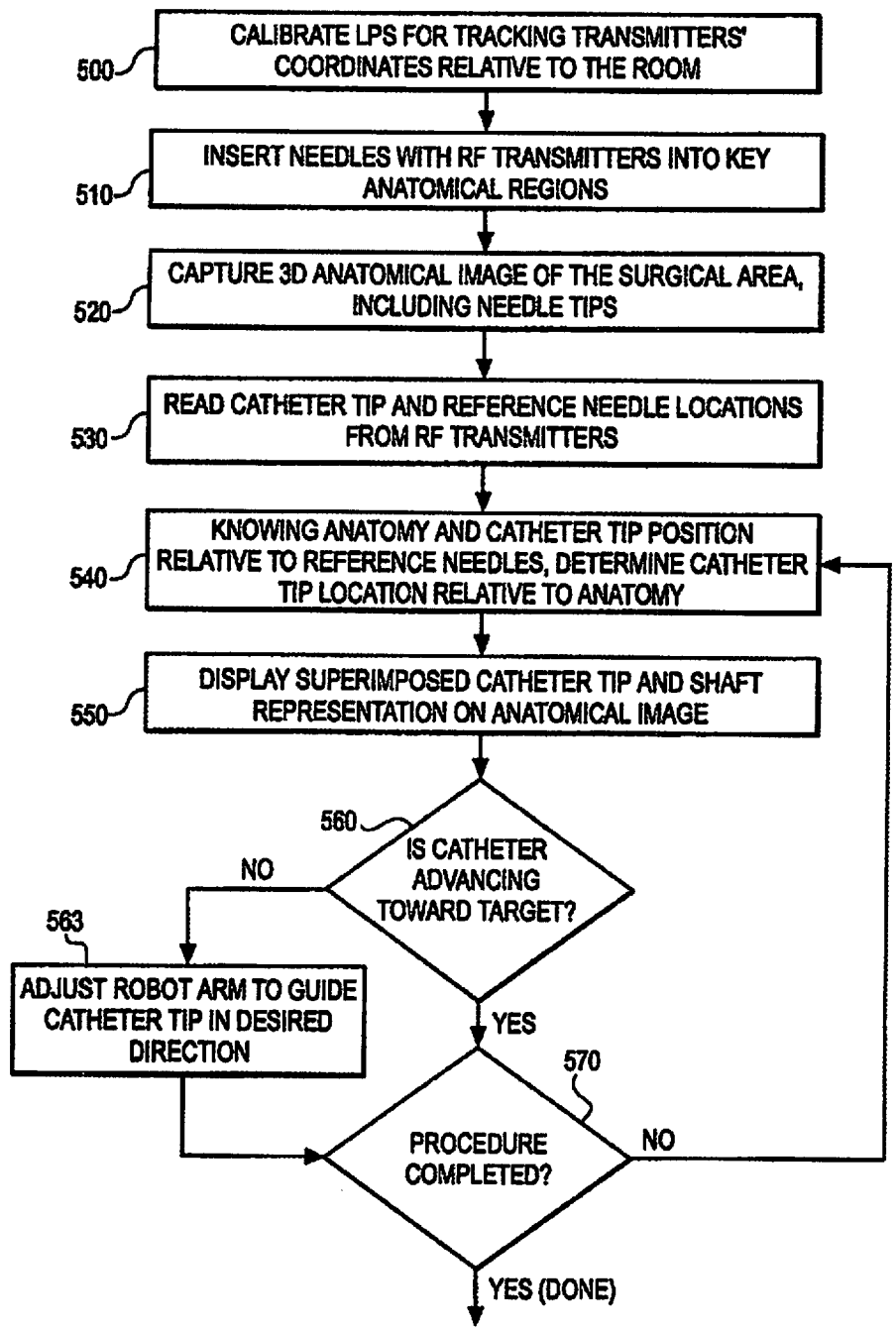
FIG. 14 is a flow chart diagram of a flexible catheter insertion procedure according to an embodiment of the present invention.

Referring now to FIG. 14, a flow chart diagram for a flexible catheter or wire insertion procedure according to an embodiment of the invention is shown. Catheters are used in a variety of medical procedures to deliver medicaments to a specific site in a patient's body. Often, delivery to a specific location is needed so a targeted diseased area can then be treated. Sometimes instead of inserting the catheter directly, a flexible wire is first inserted, over which the flexible catheter can be slid.

The distance between each of the calibrating transmitters relative to each other is measured prior to calibration step 500. Each calibrating transmitter transmits RF signals on a different frequency so the positioning sensors can determine which transmitter emitted a particular RF signal. The signal of each of these transmitters is received by positioning sensors. Since the distance between each of the calibrating transmitters is known, and the sensors can identify the signals from each of the calibrating transmitters based on the known frequency, the positioning sensors are able to calculate, using time of flight calculation, the spatial distance of each of the positioning sensors relative to each other. The system is now calibrated. As a result, the positioning sensors can now determine the spatial position of any new RF transmitter introduced into the room relative to the positioning sensors.

At step 510, reference needles that contain the RF transmitters are inserted into the body. The purpose of these needles is to track movement of key regions of soft tissue that will deform during the procedure or with movement of the patient.

Step 520, a 3D anatomical image scan, such as a CT scan, is taken of the anatomical target. Any 3D anatomical image scan may be used with the surgical robot and is within the scope of the present invention. The anatomical image capture area includes the tips of the reference needles so that their transmitters' positions can be determined relative to the anatomy At step 530, the RF signals from the catheter tip and reference needles are read.

At step 540, the position of the catheter tip is calculated. Because the position of the catheter tip relative to the reference needles and the positions of the reference needles relative to the anatomy are known, the computer can calculate the position of the catheter tip relative to the anatomy.

At step 550, the superimposed catheter tip and the shaft representation is displayed on the anatomical image taken in step 520.

At step 560, the computer determines whether the catheter tip is advancing toward the anatomical target. If it is not moving to the anatomical target, then step 563 is reached. If it is correctly moving, then step 570 is reached.

At step 563, the robot arm is adjusted to guide the catheter tip in the desired direction. If the anatomy needs to be calibrated, then the process beginning at step 520 is repeated. If the anatomy does not need to be recalibrated, then the process beginning at step 540 is repeated.

At step 570, the computer determines whether the procedure has been completed. If the procedure has not been completed, then the process beginning at step 540 is repeated.

At any time during the procedure, certain fault conditions may cause the computer to interrupt the program and respond accordingly. For instance, if the signal from the RF transmitters cannot be read, then the computer may be programmed to stop the movement of the robot or remove the flexible catheter from the patient. Another example of a fault condition is if the robot encounters a resistance above a preprogrammed tolerance level. Another example of a fault condition is if the RF transmitters on the anatomical target indicate that the location of the anatomical target has shifted relative to the RF transmitters—this spatial relationship should be fixed. In this case, one indicator that the anatomical target location has shifted relative to the transmitters is if the computer calculates that the surgical instrument appears to be inside bone when no drilling or penetration is actually occurring.

The proper response to each condition may be programmed into the, or a specific response may be user-initiated as well. For example, the computer may determine that in response to an anatomy shift, the anatomy would have to be recalibrated, and the process beginning at step 520 should be repeated. Alternatively, a fault condition may require the flowchart to repeat from step 500. Another alternative is the user may decide that recalibration from step 520 is desired, and initiate that step himself.

Figure 15A:
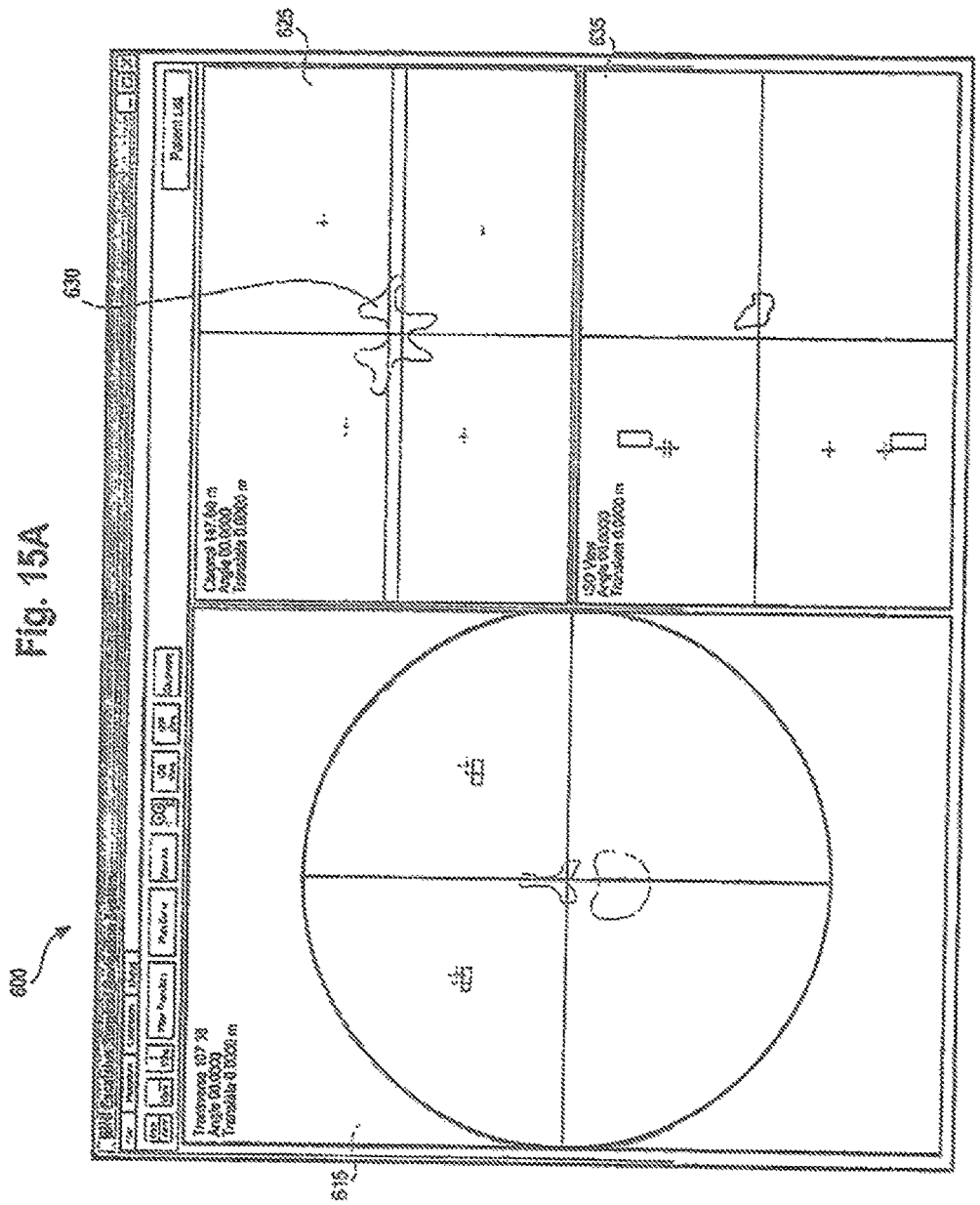
FIG. 15A shows a screenshot of a monitor display showing a set up of the anatomy in X, Y and Z views according to an embodiment of the present invention.
Figure 15B:
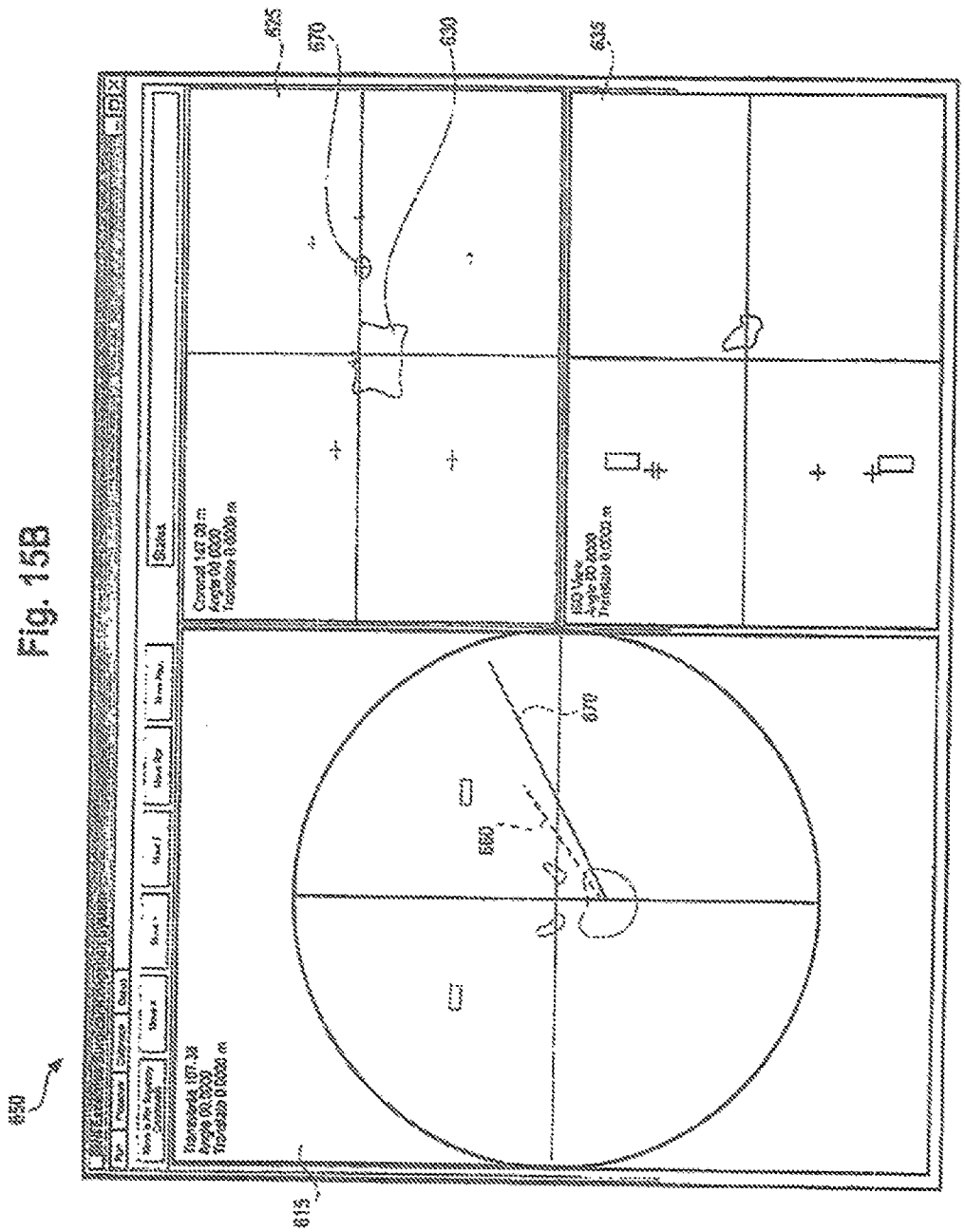
FIG. 15B shows a screenshot of a monitor display showing what the user views during an invasive procedure according to an embodiment of the present invention.

Referring now to FIGS. 15A & 15B, screenshots of software for use with an embodiment of the invention is provided. The software provides the method to select the target area of surgery, plan the surgical path, check the planned trajectory of the surgical path, synchronize the medical images to the positioning system and precisely control the positioning system during surgery. The surgical positioning system and navigation software includes an optical guidance system or RF Local Positioning System (RF-LPS), which are in communication with the positioning system.

FIG. 15A shows a screen shot 600 of the selection step for a user using the software program. Screen shot 600 includes windows 615, 625, and 635, which show a 3D anatomical image of surgical target 630 on different planes. In this step, the user selects the appropriate 3D image corresponding to anatomical location of where the procedure will occur. The user uses a graphic control to change the perspective of the image in order to more easily view the image from different angles. The user can view the surgical target 630 separate coordinate views for each of the X, Y and Z axis for each anatomical location in the database in each window 615, 625 and 635, respectively.

After selecting the desired 3D image of the surgical target 630, the user will plan the appropriate trajectory on the selected image. An input control is used with the software in order to plan the trajectory of the surgical instrument. In one embodiment of the invention, the input control is in the shape of a biopsy needle for which the user can plan a trajectory.

FIG. 15B shows a screen shot 650 during the medical procedure. The user can still view the anatomical target 630 in different x, y and z coordinate views on windows 615, 625, and 635.

In screen shot 650, the user can see the planned trajectory line 670 in multiple windows 615 and 625. The actual trajectory and location of the surgical instrument 660 is superimposed on the image. The actual trajectory and location of the surgical instrument 660 is dynamically updated and displayed.

Figure 16:
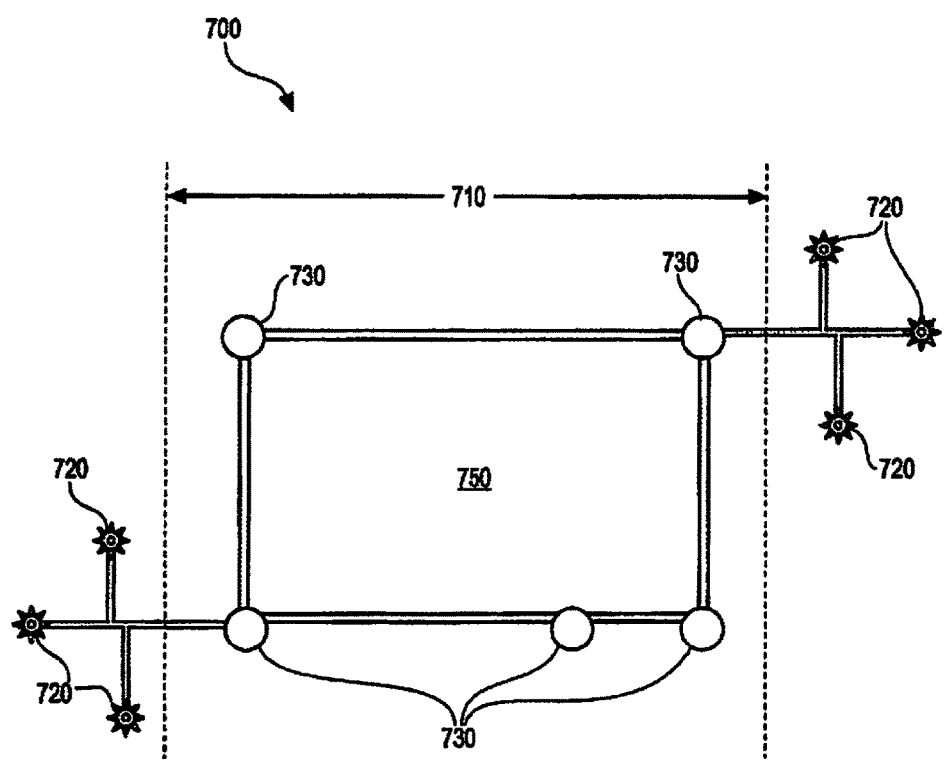
FIG. 16 shows the use of a calibration frame with the guidance system according to an embodiment of the present invention.

As described earlier, the surgical robot can be used with alternate guidance systems other than an LPS. One embodiment of the invention contemplates the use of a calibration frame for use with the guidance system, as shown in FIG. 16. A calibration frame 700 can be used in connection with many invasive procedures; for example, it can be used in thoracolumbar pedicle screw insertion in order to help achieve a more accurate trajectory position.

The use of the calibration frame 700 simplifies the calibration procedure. The calibration frame 700 comprises a combination of radio-opaque markers 730 and infrared, or "active", markers 720. The radio-opaque markers 730 are located within the CT scan region 710, and the active markers are located outside of the CT scan region 710. A surgical field 750, the area where the invasive procedure will occur, is located within the perimeter created by radio-opaque markers 730. The actual distances of the radio-opaque and active markers relative to each other is measured from a high-precision laser scan of the calibration frame. Further, active markers are also placed on the robot (not shown).

The calibration frame 700 is mounted on the patient's skin before surgery/biopsy, and will stay mounted during the entire procedure. Surgery/biopsy takes place through the center of the frame.

When the region of the plate with the radio-opaque markers 730 is scanned intraoperatively or prior to surgery in, for example, a computed tomography (CT) scanner, the CT scan contains both the medical images of the patient's bony anatomy and spherical representations of the radio-opaque markers 730. Software is used to determine the locations of the centers of the spheres relative to the trajectories defined by the surgeon on the medical images.

Because the system knows the positions of the trajectories relative to the radio-opaque markers 730, the positions of the radio-opaque markers 730 relative to the active markers 720, and the positions of the active markers 720 on the calibration frame 700 relative to the active markers on the robot (not shown), the system has all information necessary to position the robot's end effector relative to the defined trajectories.

One aspect of the software disclosed herein is a unique algorithm for locating the center of the above-described spheres that takes advantage of the fact that a CT scan consists of slices typically spaced 1.5 mm or more apart in the z direction but sampled with about 0.3 min resolution in the x and y directions. Since the diameter of the radio-opaque spheres is several times larger than this slice spacing, different z slices of the sphere will appear as circles of different diameters on each successive xy planar slice. Since the diameter of the sphere is defined beforehand, the necessary z position of the center of the sphere relative to the slices can be calculated that achieves the given set of circles of various diameters. This algorithm provides, for example, the center of a large sphere more precisely than other methods could find the center of a sphere that is closer in diameter to the slice thickness.

To provide further illustration of how the calibration plate works according to an embodiment of the invention, the steps of a closed screw/needle insertion procedure utilizing a calibration frame is described. First, a calibration frame 700 is attached to the patient's skin in the region at which surgery/biopsy is to take place. Next, the patient receives a CT scan either supine or prone, whichever positioning orients the calibration frame upward. Thereafter, the surgeon manipulates three planar views of the patient's CT images with rotations and translations. The surgeon then draws trajectories on the images that define the desired position and strike angle of the end effector.

The robot then will move to the desired position. If forceful resistance beyond a pre-set tolerance is exceeded, the robot will halt. The robot holds the guide tube at the desired position and strike angle to allow the surgeon to insert a screw or needle. If tissues move in response to applied force or due to breathing, the movement will be tracked by optical markers and the robot's position will automatically be adjusted.

As a further illustration of a procedure using an alternate guidance system, the steps of an open screw insertion procedure utilizing an optical guidance system is described. After surgical exposure, a small tree of optical markers is attached to a bony prominence in the area of interest. Calibration procedures standard for image guidance are used to establish the anatomy relative to the optical tracking system and medical images.

The surgeon manipulates three planar views of the patient's CT images with rotations and translations. The surgeon then draws trajectories on the images that define the desired position and strike angle of the end effector.

The robot moves to the desired position. If forceful resistance beyond a pre-set tolerance is exceeded, the robot will halt. The robot holds the guide tube at the desired position and strike angle to allow the surgeon to insert a screw. If tissues move in response to applied force or due to breathing, the movement will be tracked by optical markers and the robot's position will automatically be adjusted.

If desired, two or more RF transmitters can be affixed to the medical instrument at certain locations thereof, the two or more RF transmitters being selectively energizable to generate forces that are applied to the medical instrument and cause at least a portion of it to move in a desired direction. Similarly, at least three RF transmitters can be affixed to the medical instrument at desired locations thereof, if desired, the three RF transmitters being selectively energizable to generate forces that are applied to the medical instrument cause at least a portion of it to move in a desired direction. The three RF transmitters can be evenly radially distributed around the medical instrument, at a distal end of the medical instrument and/or on a leading edge of the medical instrument. From the foregoing it will be observed that numerous modifications and variations can be effectuated without departing form the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A system for performing a medical procedure, comprising:
    a robot comprising:
    an instrument;
    an effectuator element, the effectuator element configured to securely hold the instrument at a position relative to the effectuator element;
    a motor assembly that is configured to move the effectuator element in each one of the x, y and z directions; and
    a control unit that is operatively coupled to the robot,
    wherein the control unit is configured to transmit signals to the robot to cause the motor assembly to selectively move the effectuator element along the x, y and z directions without additional user input by selectively energizing a plurality of radiofrequency (RF) transmitters affixed to the instrument, the control unit being, configured (i) to calculate a position of a first transmitter of the plurality of RF transmitters by analysis of signals emitted by the first transmitter (ii) display a position of the instrument with respect to a patient's body based on the calculated position of the first transmitter and (iii) to control actuation of the motor assembly,
    wherein the control unit is configured to move the effectuator element in a direction based, at least in part, on the calculated position of the first transmitter, and
    wherein the robot includes at least one position encoder configured to determine the location of the instrument to verify the position calculated by the control unit of the first transmitter affixed to the instrument.

2. The system of claim 1, wherein a position signal is generated by the at least one position encoder to provide the location of the instrument.

3. The system of claim 2 wherein the position signal is generated with one or more of magnetic sensors, capacitive sensors, and optical sensors.

4. The system of claim 1, wherein the location of the instrument is determined relative to a reference position.

5. The system of claim 1, wherein the instrument is configured to have the first transmitter, a second transmitter of the plurality of RF transmitters, and a third transmitter of the plurality of RF transmitters radially distributed around the instrument.

6. The system of claim 1, wherein the instrument is configured to have the first transmitter, a second transmitter of the plurality of RF transmitters, and a third transmitter of the plurality of RF transmitters affixed to a distal end of the instrument.

7. The system of claim 1, wherein the instrument is configured to have the first transmitter, a second transmitter of the plurality of RF transmitters, and a third transmitter of the plurality of RF transmitters located on a leading edge of the instrument.

8. A system for performing a medical procedure, comprising:
    a robot comprising:
    an instrument positioned at a location;
    an effectuator element, the effectuator element configured to securely hold the instrument;
    a motor assembly that that is configured to move the effectuator element in each one of the x, y and z directions; and
    a control unit that is operatively coupled to the motor assembly, the control unit supplying signals to the robot to cause the motor assembly to selectively move the effectuator element along the x, y and z directions without additional user input by selectively energizing a plurality of radiofrequency (RF) transmitters affixed to the instrument, the control unit being configured (i) to calculate the position of a first transmitter of the plurality of RF transmitters by analysis of signals emitted by the first transmitter (ii) display a position of the instrument with respect to a patient's body based on the calculated position of the first transmitter, and (iii) to control actuation of the motor assembly,
    wherein the control unit is configured to move the effectuator element in a direction based, at least in part, on the calculated position of the first transmitter, and
    wherein the robot includes at least one position encoder configured to determine the location of the instrument to verify the position calculated by the control unit of the first transmitter affixed to the instrument.

9. The system of claim 8 wherein a position signal is generated by the at least one position encoder to provide the location of the instrument.

10. The system of claim 9 wherein the position signal is generated with one or more of magnetic sensors, capacitive sensors, and optical sensors.

11. The system of claim 8, wherein the location of the instrument is determined relative to a reference position.

12. The system of claim 8, wherein the instrument is configured to have the first transmitter, a second transmitter of the plurality of RF transmitters, and a third transmitter of the plurality of RF transmitters evenly radially distributed around the instrument.

13. The system of claim 8, wherein the instrument is configured to have the first transmitter, a second transmitter of the plurality of RF transmitters, and a third transmitter of the plurality of RF transmitters affixed to a distal end thereof.

14. The system of claim 8, wherein the instrument is configured to have the first transmitter, a second transmitter of the plurality of RF transmitters, and a third transmitter of the plurality of RF transmitters located on a leading edge of the instrument.

* * * * *